(12) United States Patent
Walte et al.

(10) Patent No.: US 9,753,012 B2
(45) Date of Patent: Sep. 5, 2017

(54) METHOD AND DEVICE FOR THE IDENTIFICATION OF GASES

(71) Applicant: Airsense Analytics GmbH, Schwerin (DE)

(72) Inventors: Andreas Walte, Schwerin (DE); Wolf Muenchmeyer, Ehra-Lessien (DE); Bert Ungethuem, Schwerin (DE)

(73) Assignee: Airsense Analytics GmbH, Schwerin (DE)

( * ) Notice: Subject to any disclaimer, the term of this patent is extended or adjusted under 35 U.S.C. 154(b) by 0 days.

(21) Appl. No.: 15/186,239

(22) Filed: Jun. 17, 2016

(65) Prior Publication Data
US 2016/0370321 A1    Dec. 22, 2016

(30) Foreign Application Priority Data

Jun. 19, 2015 (EP) ..................................... 15172937

(51) Int. Cl.
*G01N 27/62*    (2006.01)
*H01J 49/00*    (2006.01)

(52) U.S. Cl.
CPC ........ *G01N 27/622* (2013.01); *H01J 49/0027* (2013.01)

(58) Field of Classification Search
USPC ................................. 250/286, 287, 281, 282
See application file for complete search history.

(56) References Cited

U.S. PATENT DOCUMENTS

| 3,621,240 A | | 11/1971 | Cohen et al. |
| 4,551,624 A | * | 11/1985 | Spangler ............... G01N 27/622 250/282 |
| 5,338,931 A | * | 8/1994 | Spangler ............... H01J 49/162 250/287 |

(Continued)

FOREIGN PATENT DOCUMENTS

| DE | 10 2007 052 8 | 5/2009 |
| GB | 2 437 832 A | 11/2007 |
| WO | WO 2013/080044 A2 | 6/2013 |

OTHER PUBLICATIONS

European Search Report, corresponding to EP 15 17 2937, dated Nov. 25, 2015, 2 pages.

(Continued)

*Primary Examiner* — Kiet T Nguyen
(74) *Attorney, Agent, or Firm* — Lewis Roca Rothgerber Christie LLP

(57) ABSTRACT

Method and device for identifying gases and/or ion mobility spectrometer and method for offsetting residual humidity are provided. The object of the invention is to develop a generic method for offsetting residual humidity in an ion mobility spectrometer and a related device, which has a simple structure and which fully exploits the reduced diffusion. This is achieved by a variable drift chamber drift gas velocity, which leads to differing penetration depths of the humidity into the drift chamber, and thus to variable residual humidities in the drift chamber. Methods of this type and the associated devices for detecting and identifying gases are used to recognise and identify chemical compounds, in particular explosive materials or material compounds and/or those which are damaging to health, and which must be identified in very low concentrations.

7 Claims, 5 Drawing Sheets

(56) References Cited

U.S. PATENT DOCUMENTS

| | | | | |
|---|---|---|---|---|
| 5,968,837 A * | 10/1999 | Doring | ............... | G01N 27/622 |
| | | | | 250/281 |
| 2009/0032701 A1 * | 2/2009 | Rodier | ............... | G01N 27/622 |
| | | | | 250/282 |
| 2009/0114811 A1 * | 5/2009 | Landgraf | ............ | H01J 49/0427 |
| | | | | 250/282 |
| 2009/0114812 A1 * | 5/2009 | Landgraf | ............ | H01J 49/0427 |
| | | | | 250/282 |

OTHER PUBLICATIONS

Mayer, et al., "Accuracy of Ion Mobility Measurements Dependent on the Influence of Humidity," Analytical Chemistry 2014, 86, 5069-5076, XP055230263.

Moll, et al., "Control of dopants/modifiers in differential mobility spectrometry using a piezoelectric injector," Analyst, 2012, 137, 1458-1465, XP055230427.

* cited by examiner

METHOD AND DEVICE FOR THE IDENTIFICATION OF GASES

CROSS-REFERENCE TO RELATED APPLICATION

This application claims priority to and the benefit of European Patent Application Number 15172937.3, filed on Jun. 19, 2015, the entire content of which is incorporated herein by reference.

BACKGROUND

1. Field

The invention relates to a method for identifying gases and an associated device for identifying gases.

2. Description of Related Art

Methods of this type and the associated devices for detecting and identifying gases are used to recognise and identify chemical substances or compounds, in particular explosive materials or material compounds and/or those which are damaging to health, and which must be identified in very low concentrations.

The identification of explosive and/or toxic chemical compounds requires measuring methods with identification limits in the ppt-ppb range. In order to detect and identify these chemical compounds, spectrometers are therefore frequently used. Here, the use of ion mobility spectrometers (IMS), which are also known as plasma chromatographs, is to be preferred, since in contrast to other spectrometers such as a mass spectrometer, they are operated under atmospheric pressure and require no vacuum pump in order to generate an evacuated detection area. For this reason, IMS are small and low-cost with regard to their structural design compared to other spectrometers.

The area of application of the IMS is very wide. It ranges from the medical field, e.g. when examining the exhaled air of patients, through to use in production monitoring, e.g. when checking the quality of food products, and the military field, e.g. when identifying warfare agents. A general overview of IMS and their applications can be found for example in: G. A. Eiceman and Z. Karpas "Ion Mobility Spectrometry" (2nd edition, CRC, Boca Raton, 2005).

The structure and manner of functioning of the IMS are described in a large number of publications.

Thus, for example, in U.S. Pat. No. 3,621,240, a classic flight duration IMS is presented in which the different mobility of ions under atmospheric pressure is exploited. The target connections transferred into the IMS via an inlet system, e.g. a silicon membrane or a gas chromatography pillar, are continuously ionised in an ion source, by means of radioactive radiation, photoionisation or corona discharges. Very frequently, radioactive sources are used which directly ionise air molecules (nitrogen and oxygen). These ionised air molecules form the reactant ions $H^+[H_2O]_n$ and $O_2^-[H_2O]_n$. These reactant ions react with the interesting compounds by means of proton transfer, electron transfer or proton abstraction reactions, and form product ions $MH^+[H_2O]_n$ and $MO_2^-[H_2O]_n$. Depending on the concentration, dipole moment and humidity, dimers $M_2H^+[H_2O]_n$ are formed under high target compound concentrations, or clusters are formed under a high residual humidity which have an increased number of water molecules n.

Within a very short period of time of approx. 200 microseconds and with the aid of an electric grid, these product ions are admitted into a drift tube which comprises an electric field and which accelerates the ions in a drift gas, usually filtered air under ambient pressure. It is commonly the case that the drift gas is guided in a pneumatically close gas circuit. This drift gas circuit contains elements, e.g. filters, which purify and condition the drift gas, since the state of the drift gas has a decisive influence over the detection capabilities. A molecular sieve is used as a filter, for example, with the aid of which the humidity of the drift gas is reduced until it reaches the level of a residual humidity in the lower ppm range. Continuous filtering is necessary since ambient humidity is constantly admitted into the IMS through the inlet system, albeit at a low level.

Due to the change in polarity of the electric field of the drift track, in a positive operating mode, positive ions can be identified, and in a negative operating mode, negative ions can be identified. Due to the electric field, the admitted product ions are constantly accelerated and constantly decelerated through impacts with the neutral molecules in the drift gas. Due to the electric field, the same tensile force acts on all ions with the same charge. Since however the product ions have different masses and impact profiles, they are characterized by different drift velocities. At the end of the drift tube, the product ions hit a detector at these different drift velocities. From the different flight times of the product ions through the drift tube, which typically lie within a range of 5 to 30 milliseconds, conclusions can be drawn regarding the chemical compounds to be studied. The drift velocity can be determined from the measured flight time or drift time and the known length of the drift track. With a lesser field strength E, e.g. E=200 V/cm, the drift velocity of the product ions $v_d$ is linearly dependent on the field strength. With these lower field strengths, the mobility K of the product ions can be expressed as follows, independently of the field strength:

$$K = v_d/E.$$

Since the measurements are conducted under atmospheric pressure, the drift velocity of the ions also depends on the temperature T, the pressure p and the residual humidity in the drift tube. In order to detect and identify the chemical compounds, the mobility of the product ions is always related to normal conditions, i.e. to a normal temperature $T_0=273°$ K. and a normal pressure $p_0=1013$ hPa. Thus a temperature and pressure compensation takes place. The reduced or normalised mobility of the product ions can be shown as follows:

$$K_0 = K \cdot (T_0/T) \cdot (p/p_0) = K \cdot (273° K/T) \cdot (p/1013 \text{ hPa}).$$

However, a disadvantage with the use of the classic flying time IMS is that the residual humidity changes in the drift gas circuit. The residual humidity in the drift gas does however have a decisive influence over the detection capabilities. See also Mayer, Thomas; Borsdorf, Helko (2014): Accuracy of Ion Mobility Measurements Dependent on the Influence of Humidity. In: Anal. Chem. 86 (10), p. 5069-5076. The number n of water molecules directly influences the mass and impact profile of the cluster, its drift velocity and thus also its determined reduced mobility. With different residual humidities in the drift gas, a difference in the reduction in mobility can therefore also be anticipated. With product ions with a high level of mobility in particular, e.g. chloride ions clusters, this behaviour is clearly evident. Thus with the product ion $Cl^-[H_2O]_n$ with an average residual humidity below 1 ppm, reduced mobility of $K_0=2.80$ cm$^2$N/s can be anticipated, while with average residual humidities of 4 ppm, a reduced mobility of von $K_0=2.55$ cm$^2$/V/s can be anticipated. The reduced mobility of the product ion $Cl^-[H_2O]_n$ can thus also be regarded as a humidity indicator. Due to the different inclination of product ions to enter into clusters with water molecules, a deterioration in the differentiation of product ions can be anticipated. The probability of erroneous identifications increases. The use of residual humidity sensors here does not lead to the desired result, since on the one hand due to the low residual humidity in the lower ppm range only very expensive and large sensors such as dew point monitoring sensors can be used, while on the other, an automatic adjustment of the residual humidity is not possible.

SUMMARY

The invention is thus based on the objective of developing a method for identifying gases with an IMS and a corresponding device which has a simple, compact structure and which permits a determination as well as an adjustment of the residual humidity.

This objective is achieved by means of the method according to the features of claim 1, and by means of the device according to the features of claim 6. Advantageous embodiments are described in the features described in the subclaims.

Due to the method according to the invention for identifying gases, in which the gases to be identified are ionised and the drift times of product ions through a drift chamber are measured and the measured drift times are evaluated, wherein in order to measure the drift times the product ions are accelerated through a resulting electrical field to drift velocities in the drift chamber and a drift gas is guided into the drift chamber counter to the direction of movement of the product ions, wherein a drift gas velocity of the drift gas in the drift chamber is varied, it is advantageously possible to maintain a residual humidity in the drift chamber to a constant level. Thus, a change to the residual humidity in particular, which results due to a decrease in filter properties of the filter used, can be offset. The degree of measurement precision of the method for identifying gases is thus increased.

In a preferred embodiment of the invention, it is provided that at the same time as the drift gas velocity in the drift chamber is varied, the overall drift gas flow is also varied in order to maintain a constant drift gas velocity in a reaction chamber. As a result, it is advantageously achieved that a variation of the drift gas velocity in the drift chamber, which influences the overall gas drift flow, cannot lead to a change in the drift gas velocity in the reaction chamber. The gas to be identified is thus guided at a constant speed into the reaction chamber onto the ion inlet device. Thus, by varying the drift gas velocity in the drift chamber, the residual humidity can be very precisely adjusted.

In a preferred embodiment of the invention, it is further provided that by modifying the drift gas velocity in the drift chamber, a constant average residual humidity is set in the drift chamber. As a result, it becomes advantageously possible that due to this set constant average residual humidity, smaller residual humidity deviations in the drift chamber can be offset by varying the drift gas velocity, so that the constant average residual humidity ensues. As a result, the method for identifying gases can be conducted with a higher degree of measurement precision.

In a further preferred embodiment of the invention, it is provided that as a drift gas, water vapour in the air and/or a dopant gas in the air, in particular ammoniac or acetone, is used. To the extent that water vapour and/or dopant gas in the air are meant here, this is understood as being the gas mixture from the earth's atmosphere. When water vapour is used, the average humidity can be modified. When a dopant gas is used, such as ammoniac or acetone, the average concentration of the dopant gas can be modified, as a result of which the detection properties of the IMS can be influenced. A combined modification of average water vapour and dopant gas concentration can also be implemented.

The device according to the invention for identifying gases comprises an inlet system, at least one ion source, at least one reaction chamber and a drift chamber, which are separated by an ion inlet device, at least one screen grid and a detector and ion guidance electrons, as well as a drift gas circuit, wherein in the drift gas circuit a variable restriction is switched on so that a drift gas velocity in the drift chamber can be modified. Through this structure of the device, a simple technical means, namely the variable restriction in the drift gas circuit, can be used to vary the drift gas velocity in the drift chamber, so that a constant residual humidity is set in the drift chamber, and/or a residual humidity deviation can be offset.

In a preferred embodiment it is provided that the variable restriction is a proportional valve or a pump. These can be triggered in a simple manner and can be incorporated into a corresponding control circuit.

According to the invention, the device is also used to determine an unknown residual humidity in the drift chamber by determining a mobility of a product ions $Cl^-[H_2O]_n$ in the drift chamber. In other words, the device according to the invention can in this manner be used as a humidity sensor whereby the actual mobility of the product ion $Cl^-[H_2O]_n$ is compared with an anticipated mobility. If a reduction in mobility emerges, it can be assumed that there is a low level of residual humidity. Thus the device can be used as a humidity sensor for determining the humidity of the gases to be identified.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will now be described in greater detail with reference to an exemplary embodiment in the following figures.

DETAILED DESCRIPTION

Figure 1:
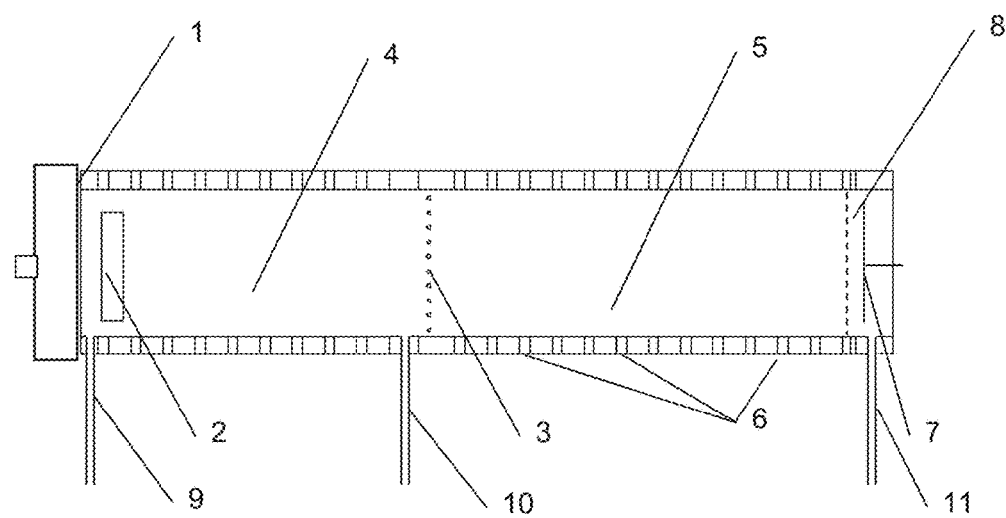
FIG. 1 shows a structure of a classic flying time ion mobility spectrometer.

FIG. 1 shows the main components of a classic flying time IMS.

The chemical compounds enter via an inlet system 1 into an ion source 2 where the ions are generated. An electrical ion gate 3 prevents the ions from entering into a drift chamber 5 from a reaction chamber 4. The electrical field strength in the drift tube (drift chamber 5) is approx. 200V/cm and is built up via corresponding electrode potentials 6. The drift tubes are usually constructed of alternating metal and insulator rings. The electrical ion gate 3 separates the reaction chamber 4, where the ion source 2 is located, from the drift chamber 5. These ion gates 3 can consist of two electrically conductive comb structures on one plane which lie on different potentials, and are also known as Bradbury-Nielsen gates. Usually, the potential difference is approx. 100V. Since the comb structures are somewhat offset locally and do not touch each other, a relatively high field force is present, so that the ions do not enter the drift tubes. By switching the ion gate 3, the potential difference is built up within several microseconds, so that the ions can enter the drift tube. The ions in the drift tube are pulled by the electrical field in the direction of a detector 7, which usually consists of a flat, conductive disc, and which is also known as a Faraday cup. A screen grid 8 is located in front of the detector 7, which serves a capacitive decoupling between the ions located shortly before the detector 7 and the detector 7. Different ions have different mobilities, so that they then arrive in temporal sequence. Due to the pole reversal of the drift tube (of the drift chamber 5), positive and negative ions are identified in alternation.

Figure 2:
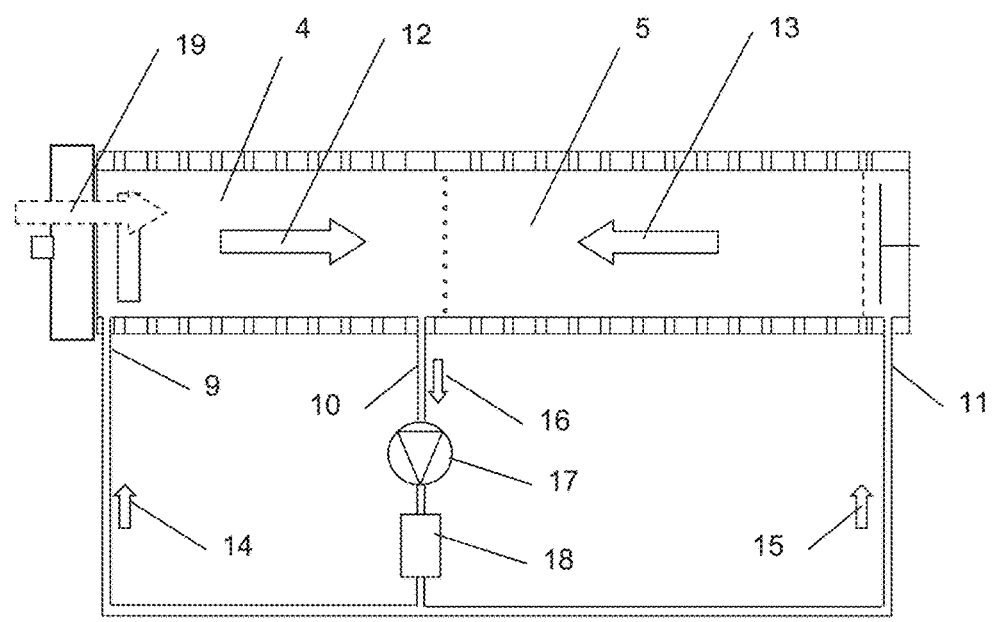
FIG. 2 shows a structure of a classic flying time ion mobility spectrometer with closed drift gas circuit according to the prior art.

FIG. 2 shows a classic flying time IMS with a closed drift gas circuit according to the prior art. The flow, in the closed drift gas circuit, is maintained by a pump 17. The drift gas 16 which flows out is suctioned out via a drift gas outlet 10 and guided through a filter 18. The drift gas is then split into two tracks, into the track 14 in which the drift gas flows into the reaction chamber 4 on the one hand, and into the track 15 on the other in which the drift gas flows into the drift chamber 5, and is respectively guided via a drift gas inlet 9 into the reaction chamber 4 or via a drift gas inlet 11 into the drift chamber 5.

Figure 3:
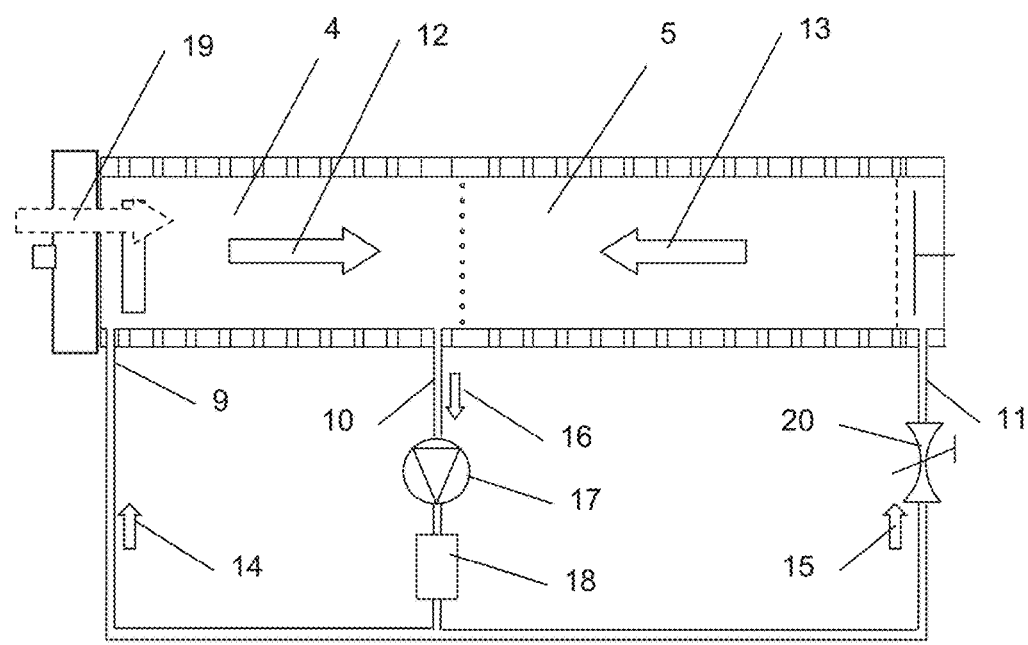
FIG. 3 shows a structure of a classic flying time ion mobility spectrometer with closed drift gas circuit according to the invention.

FIG. 3 shows a classic flying time IMS with closed drift gas circuit in accordance with the invention. The same parts as in the previous figures are assigned the same reference numerals and no repeated explanation is given. The flow, in the closed drift gas circuit, is maintained by the pump 17. The outflowing drift gas 16 is suctioned out via the drift gas outlet 10 and guided through the filter 18. The drift gas is then split into two tracks, into the track 14 in which the drift gas flows into the reaction chamber 4, and into the track 15 in which the drift gas flows into the drift chamber 5, and is guided via the drift gas inlet 9 into the reaction chamber 4 or via the drift gas inlet 11 into the drift chamber 5. In the track 15 for the inflowing drift gas into the drift chamber 5, a variable restriction 20 enables an adjustment of a drift gas velocity 13 in the drift chamber 5.

This variable restriction 20 is for example a triggerable proportional valve with which which a flow profile in track 15 can be changed. According to another example, the restriction 20 is a triggerable pump with which a flow velocity in track 15 can be changed.

Figure 4:
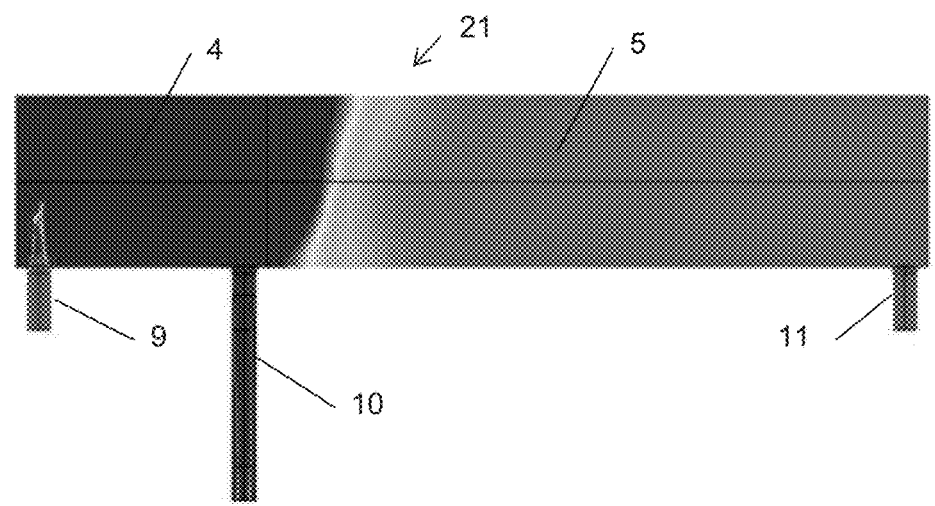
FIG. 4 shows a distribution of the humidity in an ion mobility spectrometer under constant reaction chamber and drift chamber drift gas velocity.

FIG. 4 shows the distribution of the humidity in an ion mobility spectrometer. A boundary area of the humidity boundary is labelled with the FIG. 21. The penetration depth of the humidity into the drift chamber 5 is determined by the diffusion constant of water in air and a drift gas velocity 13 in the drift chamber 5.

Figure 5:
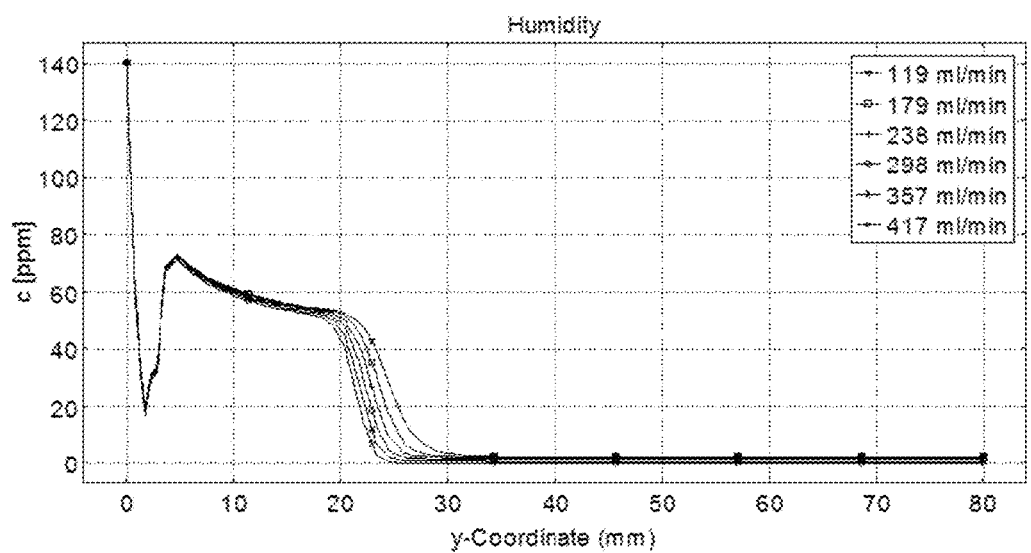
FIG. 5 shows the displacement of the humidity boundaries in the coaxial centre of an ion mobility spectrometer depending on the drift chamber drift gas velocity.

FIG. 5 shows the dependence of the penetration depth of the humidity into the drift chamber 5 on different drift gas velocities 13 in the drift chamber 5. The lower the drift velocity 13, the further the boundary area 21 is displaced in the drift chamber 5.

Figure 6:
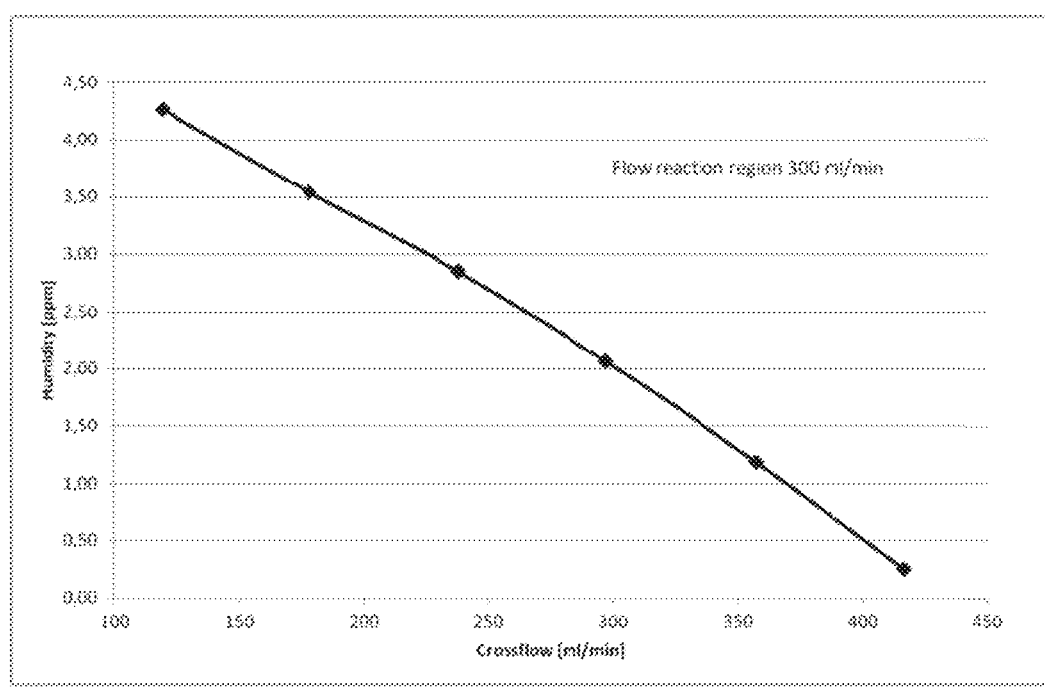
FIG. 6 shows the average residual humidity in the drift chamber depending on the drift chamber drift gas velocity.
Figure 7:
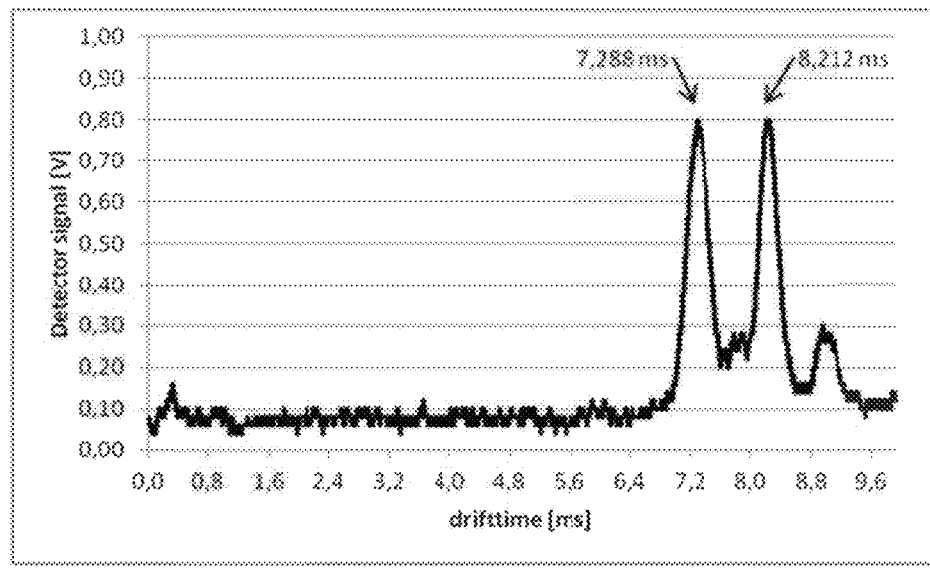
FIG. 7 shows a drift time of the $Cl^-[H_2O]_n$ (7.288 ms) and reactant ions (8.212 ms) at approximately the same reaction chamber and drift chamber drift gas velocity.
Figure 8:
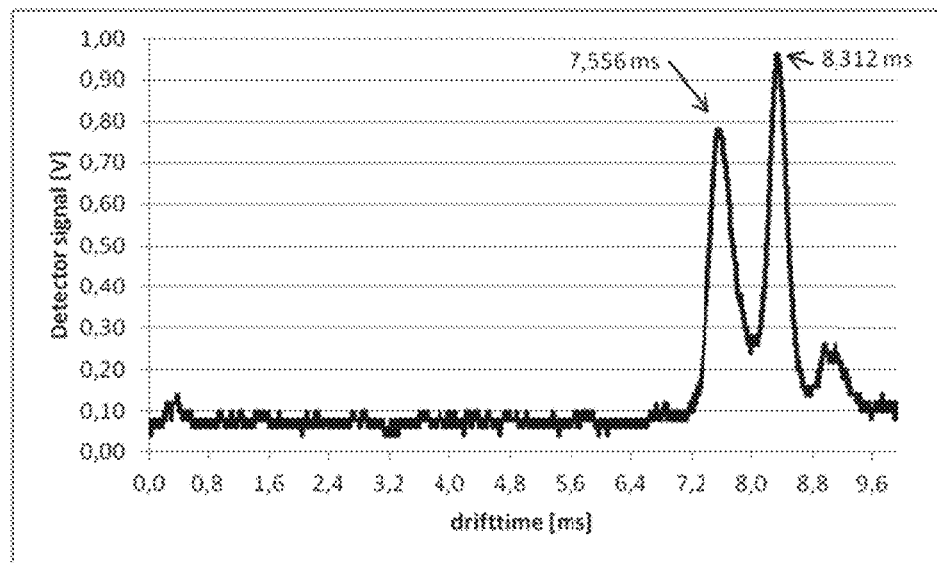
FIG. 8 shows a drift time of the $Cl^-[H_2O]_n$ (7.556 ms) and reactant ions (8.312 ms) at approximately a 40% reduced reaction chamber and drift chamber drift gas velocity.
Figure 9:
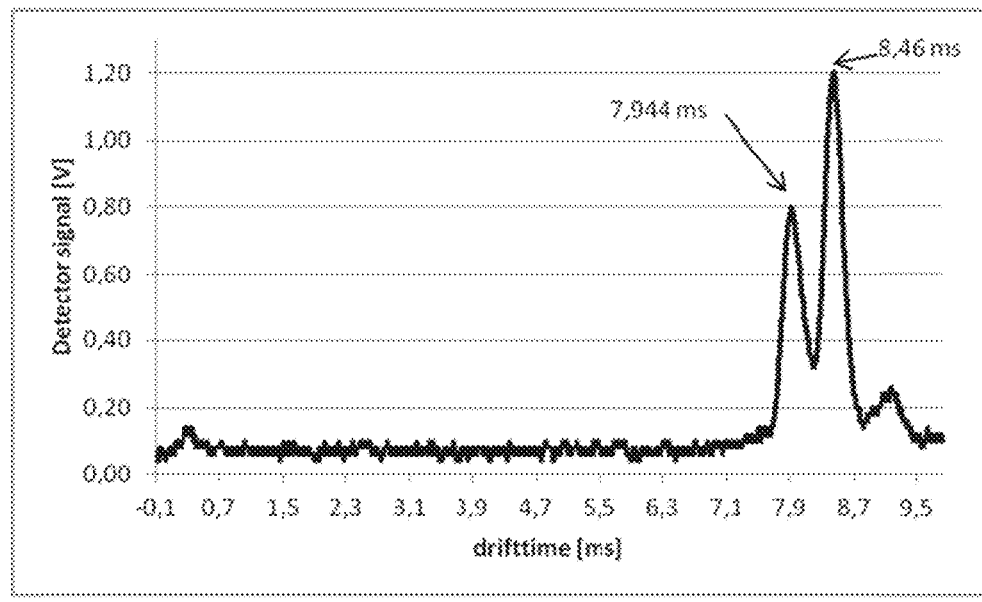
FIG. 9 shows a drift time of the Cl⁻[H$_2$O]$_n$ (7.944 ms) and reactant ions (8.46 ms) at approximately a 75% reduced reaction chamber and drift chamber drift gas velocity.
Figure 10:
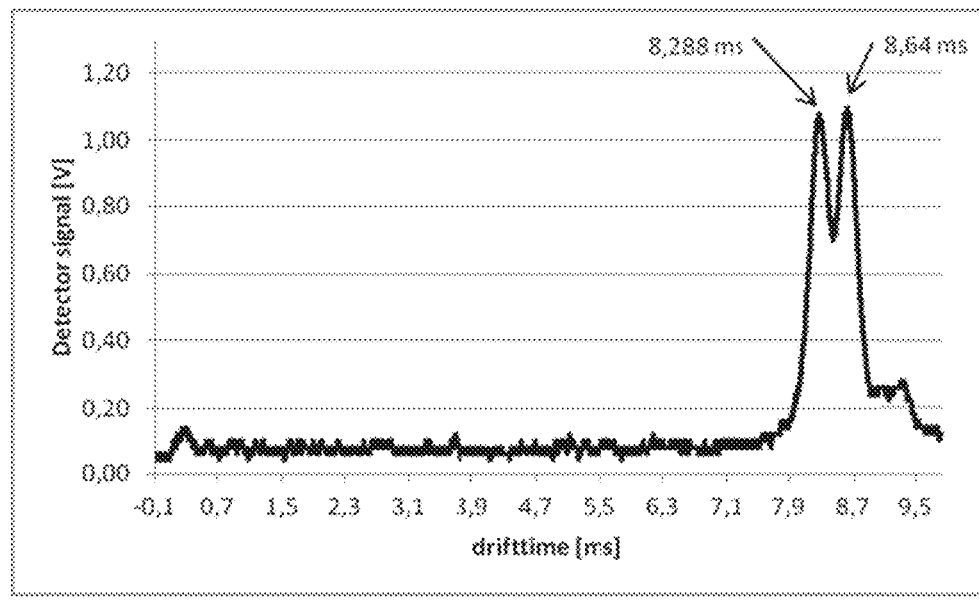
FIG. 10 shows a drift time of the Cl⁻[H$_2$O]$_n$ (8.288 ms) and reactant ions (8.64 ms) at approximately a 98% reduced reaction chamber and drift chamber drift gas velocity.

FIG. 6 shows the amount of average residual humidity in the drift chamber 5 for drift gas velocities 13 in the range of 118-410 ml/min with a constant drift gas velocity 12 of 300 ml/mm in the reaction chamber 4.

The advantage when the new method for offsetting residual humidity in an IMS is used is that it is possible to both determine the residual humidity content and continuously adjust a nominal residual humidity content. The average number of water molecules in a product ion cluster during the drift in the drift chamber 5 is dependent on the residual humidity of the drift gas 13 in the drift chamber 5. This residual humidity can by adjusted by varying the drift gas velocity 13 in the drift chamber 5. For this purpose, it is advantageous when the drift gas velocity is influenced in a targeted manner e.g. by a variable restriction 20. The residual humidity in the drift chamber 5 is determined by the humidity in the reaction chamber 4 and the humidity of the inflowing drift gas via the drift gas inlet 11. The humidity in the reaction chamber 4 is decisively determined by the ambient humidity 19, which enters the reaction chamber 4 via the inlet system 1. The humidity of the inflowing drift gas 11 is decisively determined by the filter 18. The degree of exhaustion of the filter 18 determines the ability of absorbing humidity. With progressive service life of the filter 18, less humidity is adsorbed and accordingly, the humidity of the inflowing drift gas 13 increases. Due to the diffusion of the humidity from the reaction chamber 4 into the drift chamber 5, an average residual humidity is created in the drift chamber 5. A further factor which determines the residual humidity in the drift chamber 5 is the drift gas velocity 13. The higher the drift gas velocity 13, the lower the average residual humidity in the drift chamber 5.

FIGS. 7-10 show the measurement results of an IMS constructed according to FIG. 3 with corresponding modification of the drift gas speed 13 with regard to the influence on the drift time of the chloride ion cluster (Cl⁻[H$_2$O]$_n$) and the reactant ions. Depending on the higher residual humidity in the drift chamber that ensues, a prolongation of the drift time can be detected both with the chloride ion cluster (Cl⁻[H$_2$O]$_n$) and with the reactant ions. As can be anticipated, this tendency is more clearly evident with the chloride ion cluster (Cl⁻[H$_2$O]$_n$), which leads to a merging of the chloride ion cluster (Cl⁻[H$_2$O]$_n$) with the reactant ions. With even higher residual humidities, it would no longer be possible to differentiate between these two ion species.

As used herein, the term "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The device and/or any other relevant devices or components according to embodiments of the present invention described herein may be implemented utilizing any suitable hardware, firmware (e.g. an application-specific integrated circuit), software, or a combination of software, firmware, and hardware. For example, the various components of the [device] may be formed on one integrated circuit (IC) chip or on separate IC chips. Further, the various components of the device may be implemented on a flexible printed circuit film, a tape carrier package (TCP), a printed circuit board (PCB), or formed on one substrate. Further, the various components of the [device] may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

LIST OF REFERENCE NUMERALS

Inlet system
Ion source
Ion gate
Reaction chamber
Drift chamber
Ion guide electrode
Detector
Screen grid
Drift gas inlet reaction chamber
Drift gas outlet
Drift gas inlet drift chamber
Drift gas reaction chamber
Drift gas drift chamber
Inflowing drift gas reaction chamber
Inflowing drift gas drift chamber
Outflowing drift gas
Pump
Humidity filter
Ambient humidity
Variable restriction
Boundary area

What is claimed is:

1. A method for identifying gases, the method comprising:
    forming product ions by ionizing the gases to be identified;
    measuring drift times of the product ions through a drift chamber (5); and
    evaluating the measured drift times of the product ions, wherein the measuring the drift times of the product ions comprises:
        accelerating the product ions through an electrical field to drift velocities in the drift chamber (5), and
        guiding a drift gas into the drift chamber (5) counter to a direction of movement of the product ions, wherein:
            a drift gas velocity (13) of the drift gas is varied in the drift chamber (5); and
            at the same time that the drift gas velocity (13) is varied in the drift chamber (5), an overall drift gas flow is varied to maintain constancy of a drift gas velocity (12) in a reaction chamber (4).

2. The method according to claim 1, characterized in that by modifying the drift gas velocity (13) in the drift chamber (5), a constant average residual humidity is set in the drift chamber (5).

3. The method according to claim 1, characterized in that water vapor and/or a dopant gas in the air is used as a drift gas.

4. The method according to claim 3, characterized in that ammoniac or acetone is used as a dopant gas.

5. A device for identifying gases consisting of an inlet system (1), at least one ion source (2), at least one reaction chamber (4) and one drift chamber (5), which are separated by an ion inlet device (3), at least one screen grid (8) and one detector (7) and ion guidance electrodes (6), and a drift gas circuit characterized in that in the drift gas circuit, a variable restriction (20) is switched,
    so that a drift gas velocity (13) in the drift chamber (5) and/or a drift gas velocity (12) in the reaction chamber (4) can be modified;
    wherein a mobility of a product ion $Cl^-[H_2O]_n$ in the drift chamber (5) is used for determining an unknown residual humidity in the drift chamber (5).

6. The device according to claim 5, characterized in that the variable restriction (20) is a proportional valve.

7. The device according to claim 5, characterized in that the variable restriction (20) is a pump.

* * * * *